United States Patent [19]
Lam et al.

[11] Patent Number: 5,651,943
[45] Date of Patent: Jul. 29, 1997

[54] APPARATUS AND METHOD FOR RANDOM POLYMER SYNTHESIS

[75] Inventors: Kit Sang Lam; Sydney E. Salmon, both of Tucson, Ariz.

[73] Assignee: Arizona Board of Regents, on behalf of the University of Arizona, Tucson, Ariz.

[21] Appl. No.: 273,090

[22] Filed: Jul. 11, 1994

Related U.S. Application Data

[63] Continuation of Ser. No. 795,164, Nov. 19, 1991, abandoned.

[51] Int. Cl.⁶ .................... C08F 2/00; C07K 1/04
[52] U.S. Cl. ................ 422/131; 422/134; 422/116; 530/333; 935/87
[58] Field of Search ................ 422/116, 131, 422/134, 62, 109; 935/87, 88; 530/333, 334; 435/289, 300

[56] References Cited

U.S. PATENT DOCUMENTS

| | | |
|---|---|---|
| 797,144 | 8/1905 | Nickerson . |
| 2,837,920 | 6/1958 | Keith . |
| 2,908,487 | 10/1959 | Fischer ................ 259/25 |
| 3,071,969 | 1/1963 | Cline et al. ............ 73/421 |
| 3,188,058 | 6/1965 | Locke ................ 259/89 |
| 3,343,813 | 9/1967 | Török et al. .......... 259/3 |
| 3,489,306 | 1/1970 | Bubb ................ 215/6 |
| 4,387,998 | 6/1983 | Szigeti ............ 366/130 |
| 4,668,476 | 5/1987 | Bridgham et al. .... 422/62 |
| 4,671,941 | 6/1987 | Niina et al. ........ 422/131 |
| 4,701,304 | 10/1987 | Horn et al. ........ 422/62 |
| 4,704,256 | 11/1987 | Hood et al. ........ 422/68 |
| 4,746,490 | 5/1988 | Saneii ............. 422/62 |
| 4,873,103 | 10/1989 | Cordera ........... 426/233 |
| 5,053,454 | 10/1991 | Judd ............. 525/54.11 |
| 5,182,366 | 1/1993 | Huebner et al. ..... 530/334 |
| 5,252,296 | 10/1993 | Zuckermann et al. .. 422/116 |

OTHER PUBLICATIONS

14th International Congress of Biochemistry, Abstracts, "Area 1: Proteins and Nucleic Acids in Three Dimensions", Jul. 15, 1988, vol. V.

Lam et al., "A new type of synthetic peptide library for identifying ligand–binding activity", Nature, vol. 354, Nov. 7, 1991.

Furka et al., "General method for rapid synthesis of multicomponent peptide mixtures", Int. J. Peptide Protein Res. 37, Jun. 1991, 487–493.

*Primary Examiner*—Christopher Kim
*Attorney, Agent, or Firm*—Pennie & Edmonds

[57] ABSTRACT

An apparatus and method are provided for the synthesis of compounds, e.g., oligomers or polymers, by the repeated steps of coupling various subunits onto solid supports. The apparatus has for a first member a vessel having chambers opening to a surface of the member, and has for a second member a vessel having a single chamber opening to a surface of the second member. The chambers preferably have filtered apertures to permit passage of gas or liquid while retaining the solid supports in the chambers. The first member is joined with the second member, forming a pair, such that the openings of the first member open into the second member. The first member is used for synthesis reactions and for holding unmixed compounds coupled to solid supports. The second member is used for mixing the solid supports. The solid supports are transferred from one member to another, e.g., by inverting the pair. The chambers of the first member are arranged such that transfer of compound coupled to solid supports from the first member to the second redistributes in a substantially uniform manner.

16 Claims, 4 Drawing Sheets

APPARATUS AND METHOD FOR RANDOM POLYMER SYNTHESIS

This is a continuation of application Ser. No. 07/795,164, filed Nov. 19, 1991, abandoned.

This invention was made with government support under NIH Contract Nos. CA 17094 and CA 23074 awarded by the National Cancer Institute/National Institutes of Health. The government has certain rights in the invention.

FIELD OF INVENTION

This invention relates to an apparatus and a method for the synthesis of all possible combination of compounds made up of individual subunits, e.g., oligomers or polymers. The invention is directed in particular to an apparatus for the synthesis of compounds formed on solid supports by repeated steps of coupling, mixing and redistributing. The invention also relates to a method for synthesizing a library of polymers, which comprise many or all possible combinations of species of subunits, using said apparatus.

BACKGROUND OF THE INVENTION

A simplified apparatus for the synthesis of a plurality of compounds, e.g., oligomers or polymers, is desired for many applications.

For example, in the art of peptide synthesis, there is a need for a device to simply and quickly synthesize anywhere from a few thousand to several million truly random peptide sequences. Houghton (Houghton, R. A. *Proc. Natl. Acad. Sci.* 82:5131–5135 (1985)) employees a "tea bag" method using standard Boc amino acid resin in polypropylene mesh packets with standard deprotecting, neutralization, coupling and wash protocols of the original solid phase procedure of Merrifield, R. B., *J. Amer. Chem. Soc.*, 85:2149–2154 (1963). Hundreds of peptides were synthesized simultaneously. Geysen et al. (*Molecular Immunology* 23: 709–715 (1986)) systematically synthesized peptides on polyethylene rods in a relatively short time. Geysen employed a microcomputer program to direct the once-a-day addition of the correct amino acid to the correct rod.

The Advanced Chemtech ACT Model 350 Peptide Synthesizer is capable of concurrently synthesizing up to 96 peptide sequences in up to 96 respective reaction chambers. The apparatus is not capable of concurrently synthesizing larger numbers of peptide sequences, and also requires the number of reaction chambers to at least equal the number of peptide sequences to be synthesized. These various techniques are capable of generating only a hundred to a few thousand peptides at a time.

Thus, there is a need in the art for an apparatus to quickly synthesize several thousand to several million substantially random peptide sequences in which a single peptide species can be readily and quickly isolated. Such a collection of peptide sequences would assist in the development of agents that could block, promote, or otherwise affect cellular reactions that involve recognition and binding. These agents would be useful in the treatment or diagnosis of a number of diseases. Similarly, knowledge of the peptide sequence greatly facilitates the study of the antibody-antigen reaction. More importantly, however, knowledge of the peptide sequence makes it possible to synthesize peptides that can be used as diagnostic and therapeutic agents.

It is an object of the present invention to provide an apparatus for forming a plurality of compounds formed on solid phase supports by repeatedly coupling various subunits onto solid supports followed by the randomization and redistribution of these samples.

It is a still further object of the present invention to provide an automated apparatus to synthesize this plurality of polymers.

SUMMARY OF THE INVENTION

The present invention provides an apparatus for mixing and redistributing compounds coupled to solid supports. The apparatus includes a first vessel having a plurality of chambers for holding aliquots of compounds coupled to solid supports, termed a reaction vessel. The chambers of the reaction vessel open to a surface of the vessel. A second vessel has a single chamber of sufficient volume to hold all compounds coupled to solid supports in the chambers of the reaction vessel and to permit mixing and randomization of the compounds coupled to solid supports. The second vessel, termed the mixing vessel, has an opening to the chamber. The reaction vessel contacts the mixing vessel, forming a pair of vessels, such that all openings of the reaction vessel face the opening of the mixing vessel. The pair of vessels are invertible to permit transfer of compounds coupled to solid supports from the chambers of the reaction vessel to the chamber of the mixing vessel, and permitting transfer and substantially uniform redistribution of compounds coupled to solid supports from the chamber of the mixing vessel to the chambers of the reaction vessel.

A method of synthesizing a plurality of compounds utilizing the apparatus is also provided.

BRIEF DESCRIPTION OF THE DRAWINGS

The nature, advantages, and various other additional features of the invention will appear more fully upon consideration of the illustrative embodiments now to be described in detail in connection with the accompanying drawing figures, wherein.

DETAILED DESCRIPTION OF THE INVENTION

Figure 1:
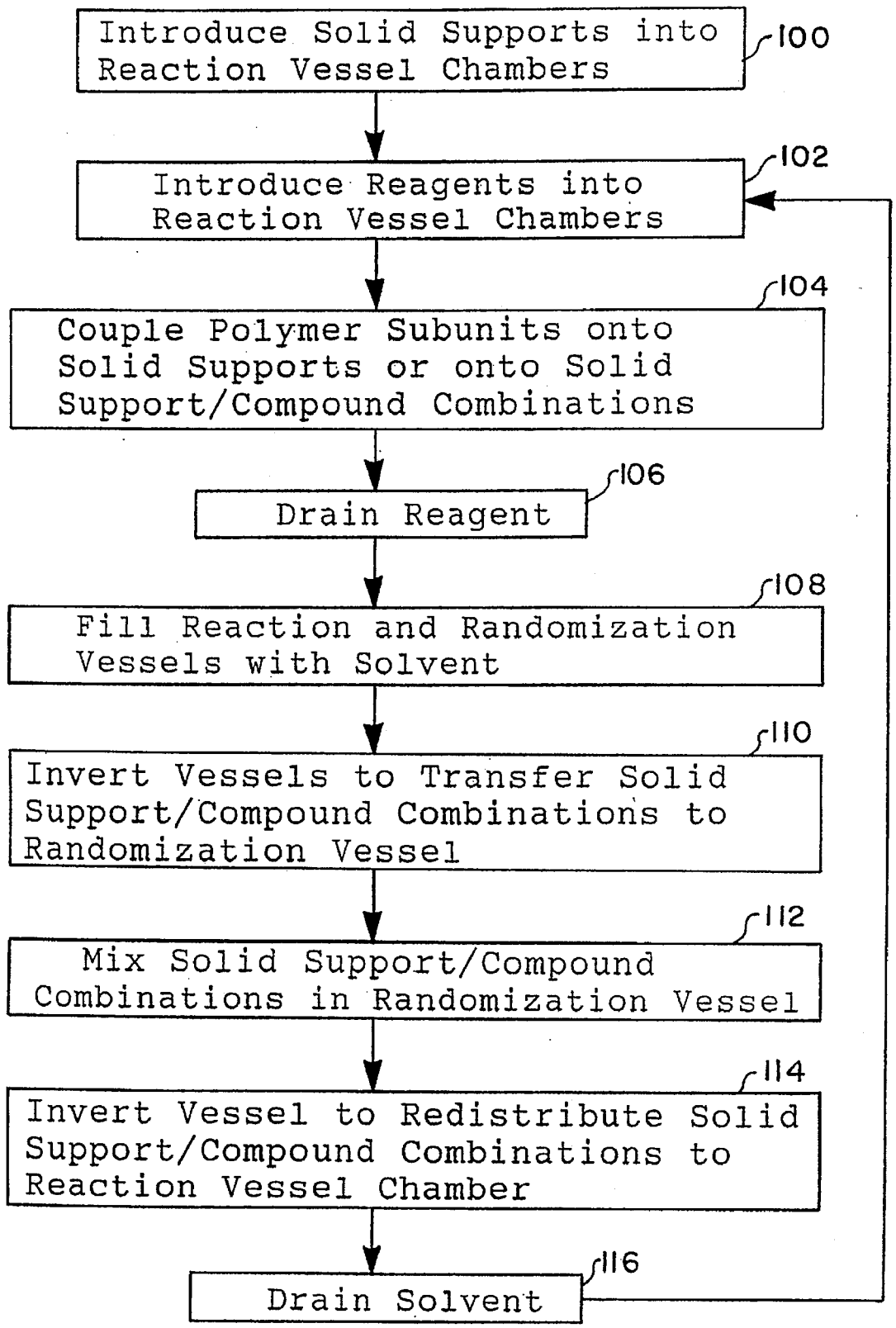
FIG. 1 is a block diagram illustrating the major steps for utilizing the apparatus of the invention.

The invention relates to an apparatus for mixing and redistributing compounds, such as polymers comprising coupled subunits, coupled to solid supports. The apparatus comprises a first member comprising a vessel having a plurality of chambers, herein referred to as "reaction chambers," for holding aliquots of compounds coupled to solid supports, wherein each of the chambers opens to a same surface of the vessel. The first vessel is referred to herein as the "reaction vessel." The number of reaction chambers will correspond to at least the number of different subunits to be coupled in any given step. The apparatus also comprises a second member comprising a vessel having a first surface and having a chamber, herein referred to as the "mixing vessel." The mixing vessel has sufficient volume to both hold all compounds coupled to solid supports of the first member and permit mixing of the compounds coupled to solid supports. The mixing vessel also has an opening to the first surface of the vessel. The first member is in contact with the second member to form a pair of vessels arranged such that all openings of the first member face the opening of the second member. The pair of vessels are invertible to permit transfer of compounds coupled to solid supports from the chambers of the first member to the second member, and also permit transfer and substantially uniform distribution of compounds coupled to solid supports from the second member back to the chambers of the first member.

The reaction vessel of the first member preferably comprises a block of non-reacting material, such as Teflon, which is either molded, cast or drilled to comprise a plurality of chambers of substantially equal volume. Alternative materials include Kevlar, polypropylene or cast glass.

The chambers of the first member are preferably of triangular or pie-slice shaped cross-section, with each chamber having a vertex adjacent to at least one vertex of all other chambers. Alternatively, the chambers may be of a right circular cylindrical tube shape, though other shapes that permit uniform redistribution are also possible. Additionally, fitted pegs may be inserted into the chambers to block off unnecessary chambers in a particular synthesis. Preferably, the fitted peg extends into the chamber of the mixing vessel so that upon redistribution of the solid support/subunits into the reaction chambers no solid support is retained on the blocked reaction chamber, and the redistribution will be even.

Preferably, each reaction chamber also has at least one aperture in addition to the opening at the vessel's first surface into which liquids or gases may be introduced or removed. Each aperture has a filter to retain solid phase supports while allowing liquids and gasses to flow. Filters for use in the apparatus include but are not limited to sintered glass, polyethylene frits, polypropylene frits, teflon frits, etc. When each reaction chamber has an aperture, at least one valve is provided to control the flow of gas or liquid to and from the aperture. The valve is preferably a solenoid valve. Alternatively, a peristaltic pump may be used to introduce liquids or gases into the chambers and to remove liquids from the chamber. Other types of valves or pumps may also be used.

The mixing vessel of the second member preferably has a right circular cylindrical shape where the opening forms one end of the right circular cylindrical shape. The chamber has at least one aperture and each aperture has a filter to retain the solid supports while permitting liquid and gas flow. The chamber also is, preferably, connected to a valve to control the flow of gas or liquid into the chamber and to vent the chamber. Mixing means, such as a magnetic or mechanical stirrer, can be provided in the mixing vessel.

The apparatus may also be provided with the capability for controlling temperature, e.g., to either maintain a constant reaction temperature, or to raise or lower the reaction temperature. Temperature may be controlled by permitting cooling or heating fluids to pass through spaces around the reaction chambers of the first member. Alternatively, the member may be surrounded by an incubator, a thermal jacket a thermocouple, or other means of controlling temperature.

The steps of introducing liquids and/or gases, removing liquids and inverting the pair of vessels may be controlled manually. In a more preferred embodiment, a horizontal rod is attached at one end of the pair of vessels orthogonally to an axis of the vessels, and a motor attached to the rod for rotating the pair of vessels about the axis such that the pair of vessels may be inverted by rotation about the axis. Additionally, microcomputer control means or other automated control means of these operations may be provided.

Using this apparatus, a plurality of compound such as polymers may be formed in the following manner: A plurality of solid supports are first divided into at least two fractions, i.e., aliquots, and introduced into the reaction chambers of the first member. The terms "fraction" and "aliquot" as used herein are synonymous and are used interchangeably. A first set of subunits are introduced to the aliquots of solid supports in the reaction chambers.

As used herein, a solid support is not limited to a specific type of support. However, a solid support will be inert to the particular coupling reaction, and will comprise reactive groups for coupling to a subunit of the compound to be synthesized. A large number of supports are available and are known to one of ordinary skill in the art. Solid supports include silica gels, resins, derivatized plastic films, glass beads, cotton, plastic beads, alumina gels. A suitable solid support may be selected on the basis of desired end use and suitability for various synthetic protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California). In a preferred embodiment for peptide synthesis, solid support refers to polydimethylacrylamide resin.

Subunits for use in the invention have one reactive functional group. The functional group will react with a group on the solid phase support, but not with a group on any other subunit. For example, if the functional group on the subunit is an electrophile it will react with a nucleophilic group on the solid support. Other reactive pairs, e.g., Lewis acid—base pairs, are well known in the art. In any reaction step, only one new subunit will couple to a single group on the solid support, although the solid support may contain more than one group capable of reacting with the functional group on the subunit.

The first set of subunits are completely coupled to each of the solid supports to form a solid support/first set of subunits combination. That is, a subunit is coupled to substantially every group on the solid support capable of reaction with the functional group on the subunit. After the coupling reaction is complete, the fraction can be washed and the extent of coupling tested, if that is desired. In a specific embodiment, the polymer is a peptide, and the completeness of coupling is tested by the ninhydrin method. If deprotection of reactive groups for the next coupling step is necessary, that can be done at this point, or in the mixing vessel or after redistribution. The pair of vessels are then inverted to transfer the fractions of solid supports/first set of subunits into the mixing vessel of the second member. The fractions of the solid support/first set of subunits are then thoroughly mixed. Preferably the fractions are mixed by repeatedly inverting the first and second vessels. In other embodiments, the fractions can be mixed in the mixing vessel with a magnetic or mechanical stirrer, or by vigorously bubbling an inert gas, or by shaking. Any other means known in the art of thoroughly mixing fractions of solid support can be used, and are considered as within the scope of the invention.

The resulting mixture is divided into at least two fractions by filling with liquid and again inverting the pair of vessels to permit substantially uniform redistribution of solid support/first set of subunits into the chambers of the first member. The liquid is removed and a second set of subunits separately introduced to the fractions. The second set of subunits are also completely coupled to the solid phase/first set of subunits combinations to form a compound containing a first subunit and a second subunit attached to a solid support.

The apparatus provides for introduction of deprotection reagents to cleave protecting groups from the solid support/ compound reactive group, and for introduction of solvents to wash the solid support, as necessary for a particular synthesis.

To couple additional subunits onto the compound, the following steps are then repeated: the pair of vessels are inverted, transferring the fractions of solid supported subunit combinations into the chamber of the second vessel. The fractions of the newly formed solid support/subunits combinations are thoroughly mixed. The resulting mixture is then redistributed into at least two fractions by filling with liquid and again inverting the pair of vessels to permit substantially uniform transfer of solid support/subunit combinations into the chambers of the first vessel. The liquid is then removed and an additional set of subunits separately introduced to the fractions, completely coupling the additional set of subunits to substantially all solid supports/ subunit combinations to form a compound attached to a solid support comprising a sequence of all the subunits introduced.

Preferably, the number of solid supports corresponds to at least the number of compounds to be synthesized.

This method can be repeated as many times as the length of compound chosen. For example, if compounds comprising five subunits are desired, the method is repeated five times. Through these repeated steps, various species comprising random combinations of subunits are formed on the solid supports. The same species of reagent are introduced into a particular chamber in each reaction step, thus minimizing the complexity of introducing fluids.

Significantly, the method of the instant invention allows the synthesis of polymers such that each solid support will contain only one species of polymer. The polymer species can then be screened for a particular activity. A solid support/polymer combination that demonstrates the desired activity can be isolated. Isolation of a solid support/polymer combination is much more straightforward than isolation of a single polymer from a multimode of polymer species, e.g., when all the polymer species are in a homogeneous mixture. In specific embodiments, the polymer is a peptide or an oligonucleotide, and a biological activity is detected, e.g., as described in copending U.S. applications Ser. No. 07/546, 845 and Ser. No. 07/717,454, incorporated herein by reference in their entirety.

In a preferred embodiment, an apparatus may be used for synthesizing a plurality of compounds coupled to solid supports, wherein the first means is coupled to the second means, permitting transfer of compounds coupled to solid supports from the first means to the second means and permitting transfer and substantially uniform redistribution of compounds coupled to solid supports from the second means to the first means.

5.1 DESCRIPTION OF THE PREFERRED EMBODIMENT

Referring to FIG. 1, there is illustrated a block diagram of a method for synthesizing a plurality of compounds. The method comprises dividing a plurality of solid supports into fractions (i.e., aliquots) and introducing the fractions into chambers of a first vessel, the reaction vessel (100). The first vessel has a plurality of chambers, the reaction chambers, each chamber receiving a fraction of solid supports. A second vessel having a single chamber, the mixing vessel, is opposedly affixed to the first vessel so that openings of the chambers of the reaction vessel open to the opening of the mixing vessel. The reagent, a first set of subunits of the compounds, are separately introduced to the fractions of solid supports in the reaction chambers (102). The subunits are completely coupled onto solid supports or onto solid support/compound combinations (104). Preferably the reagent is drained (106), and the solid supports washed. The pair of vessels are inverted to transfer the fractions of solid support/compound into the randomization vessel (110); transfer is facilitated by filling both vessels with solvent prior to inverting them (108). The fractions of the solid support/compound combinations are thoroughly mixed in the randomization vessel (112). The random mixture of solid supports is divided into fractions by filling all of the chambers with liquid and again inverting the pair of vessels to permit substantially uniform redistribution of solid support/ compound combinations into the chambers of the reaction vessel (114). Solvent is drained (116) and the process repeated by the addition of reagents into the separate chambers of the reaction vessels.

Figure 2:
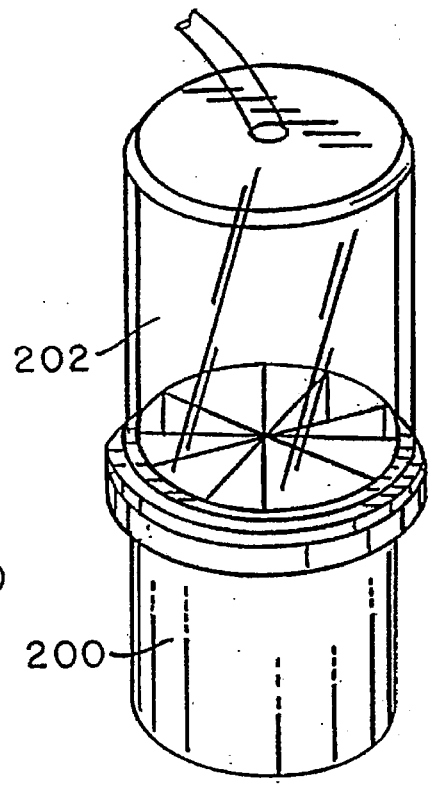
FIG. 2 is a perspective view of the preferred embodiment of the present invention.

Referring to FIG. 2, there is illustrated an apparatus for synthesizing a plurality of polymers, comprising a first member comprising a reaction vessel 200 and a second member comprising a mixing vessel 202.

Figure 3:
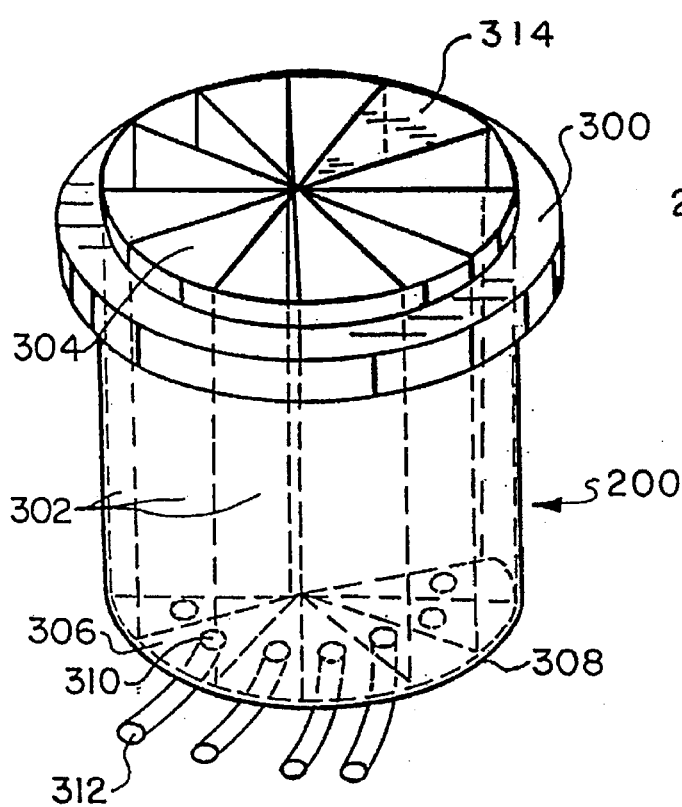
FIG. 3 is an enlarged perspective view of the reaction vessel illustrated in FIG. 2.
Figure 4:
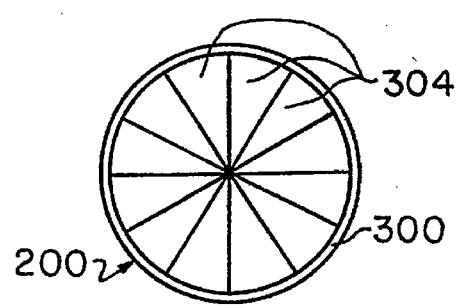
FIG. 4 is a plan view of the reaction vessel of FIG. 3.
Figure 5:
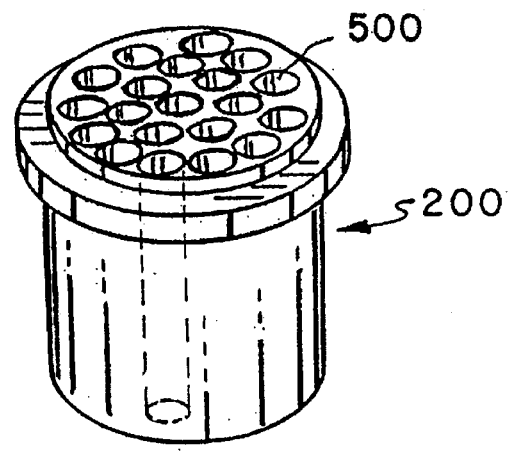
FIG. 5 is a perspective view of an alternative embodiment of the reaction vessel.

Referring now to FIG. 3, a reaction vessel 200 is preferably of cylindrical shape and is provided with a lip 300 which is configured and dimensioned to support mixing vessel 202. The reaction vessel also comprises a plurality of reaction chambers 302 which are of triangular or pie-slice shaped cross-section to allow substantially uniform redistribution of solid supports after the mixing step. The reaction chambers 302 have an open end 304 and also have a closed end 306 at the base 308 of reaction vessel 200. One or more chambers which are unnecessary in a particular synthesis may be blocked off, such as by inserting of a fitted peg 314. Each closed end 306 has a filtered aperture 310 connected to tubing 312. FIG. 4 is a plan view of reaction vessel 200 showing open end 304. In an alternative embodiment, shown in FIG. 5, the reaction vessel chambers 500 are of a right-circular cylindrical tube shape.

Figure 6:
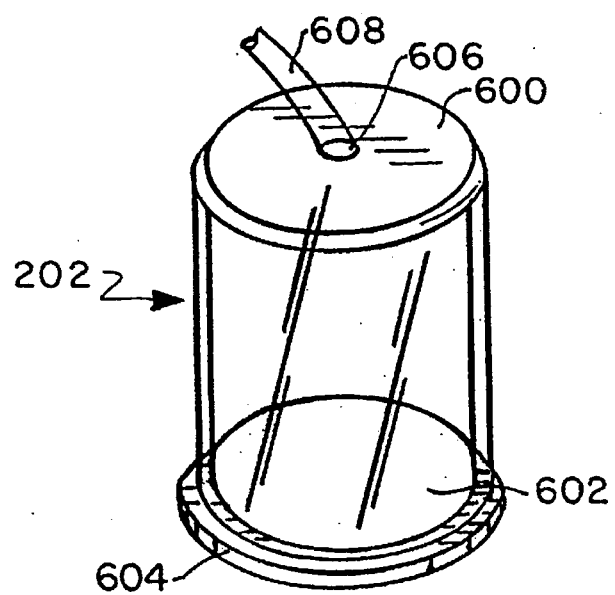
FIG. 6 is an enlarged perspective view of the mixing vessel illustrated in FIG. 2.

Referring now to FIG. 6, mixing vessel 202 is also of right circular cylindrical shape with a flat closed end 600. Opposite closed end 600 is an open end 602 having a lip 604 which can contact lip 300 of reaction vessel 200. Reaction vessel 200 may be secured to mixing vessel 202 by clamping lip 300 to lip 604 using standard clamps known in the art. To insure a seal against loss of liquids, an O-ring may be used between lips 300 and 604, or, alternatively, the two lips may have interlocking grooves or other sealing means. Closed end 600 of mixing vessel 202, is provided with a filtered aperture 606 which permits the input of inert gas or liquid and allows venting of the vessels through tube 608. Aperture 606 is filtered to prevent the loss of solid supports during mixing and randomization.

Figure 7:
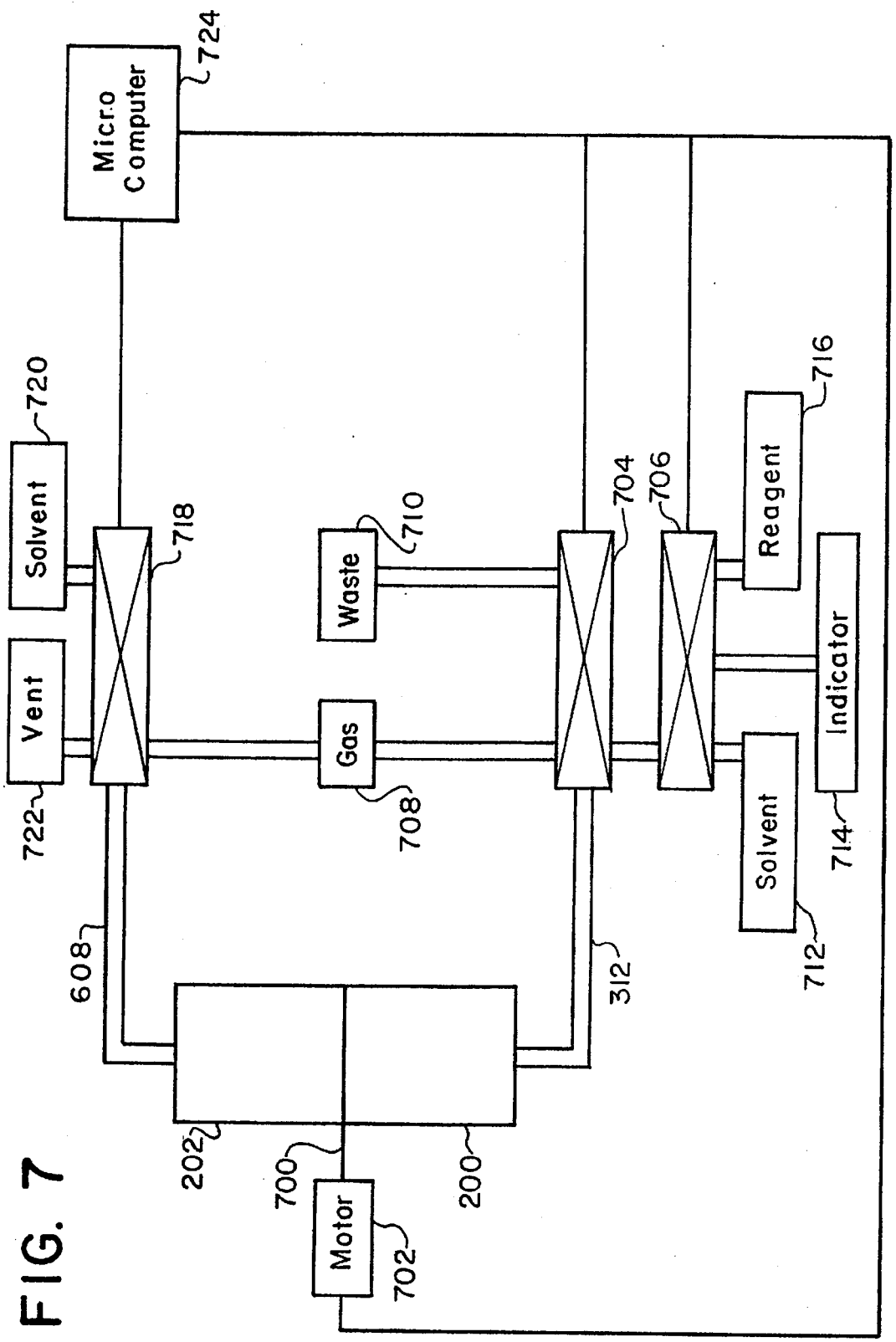
FIG. 7 is a perspective view of a preferred embodiment.

Referring now to FIG. 7, transfer of materials between reaction vessel 200 and mixing vessel 202 is effected by rotating the two vessels about pivot 700 to invert the vessels. Rotation may be effected by a motor 702 or, alternatively, may be effected manually.

Gases and liquids are introduced into chambers 302 of reaction vessel 200 and liquid waste is removed from the chambers using an arrangement of four-position solenoid valves. A first solenoid valve 704, preferably a four-position solenoid valve, is connected to a reaction chamber via tubing 312. First position solenoid valve 704 may be positioned in an off position, in which there is no input or output, or may be positioned to open to a gas input positive 708 so that gas is fed into chambers 302. Alternatively, first position solenoid valve 704 may be positioned to open to a wastes output 710, to allow removal of liquid wastes, or may be positioned to open to second solenoid value 706. Second solenoid valve 706 is also preferably of four-position type and may be positioned in an off position, or positioned to open to a solvent input 712, to open to an indicator input 714, or to a reagent input 716. Reagents and solvents are fed under pressure to the second solenoid valve, preferably via tubing, and are pressurized using an inert gas.

Using the above arrangement, gas, solvent, indicator, or reagent may be supplied to reaction chambers 302 or wastes may be removed therefrom. To introduce gas into a chamber, first solenoid valve 704 is opened to gas input 708. To introduce solvent, indicator, or reagent, first solenoid valve 704 is opened to second solenoid valve 706, and second solenoid valve 706 is opened to the respective input. After input of reagents into reaction chambers 302, tubing 312 is purged of any remaining reagent by flushing the tubing with solvent into reaction vessel. Two solenoid valve arrangements are present for each chamber in reaction vessel, and all inputs for each chamber are identical except, possibly, for the species of reagent.

To introduce solvent or gas into mixing vessel 202 or to vent the vessel, solenoid valve 718 is connected to mixing vessel 202 via tubing 608. Solenoid valve 718 is preferably a four-position solenoid valve. Solenoid valve 718 may be positioned in the off position, in which no input or venting occurs, or may be opened to a solvent input 720, connect to gas 708, or vented to atmosphere 722.

To remove liquids from reaction vessel 200 and from mixing vessel 202, mixing vessel solenoid valve 718 is opened to gas position 708 while first solenoid valves 704 of all reaction chambers 302 are opened to waste position 710, thus causing the draining of all liquids.

To introduce liquids into reaction chambers 302 (and mixing vessel 202), first solenoid valve 704 of reaction chambers 302 are opened to the second solenoid valve 706 and second solenoid valve 706 is in turn opened to the desired liquid. At the same time, the mixing vessel solenoid valve 718 is opened to the vent position 722.

To cause stirring during a reaction, the reaction chambers 302 are only partially filled with liquid. First solenoid valve 704 of each reaction chamber 302 is then opened to gas input position 708 while the mixing vessel solenoid valve 718 is opened to the vent position 722. In this manner, gas may bubble through liquids in reaction chambers 302 to agitate and thereby stir the liquids.

Operation of the solenoid valves 704, 706, 718 and motor 702 may be controlled manually or by a microcomputer 724. Microcomputer 724 may be interfaced to solenoid valves 704, 706, 718 and motor 702 using input-output cards, as is known in the art. FIG. 1 discloses an example of a series of rudimentary operations to couple subunits onto solid supports or onto solid support/subunit combinations, followed by mixing, randomization, and redistribution. Using a programming language known in the art, these rudimentary operations may be translated into instructions to program a microcomputer to control these operations and therefore control the synthesis of a plurality of polymers.

5.2 SYNTHESIS OF A PEPTIDE LIBRARY USING THE APPARATUS

The present invention provides a preferred apparatus for the synthesis of a peptide library comprising all possible sequences of peptides.

In one embodiment, a library of pentapeptides comprises 19 of the 20 common (eukaryotic) amino acids excluding cysteine: alanine, arginine, asparagine, aspartic acid, glutamic acid, glutamine, glycine, histidine, isoleucine, leucine, lysine, methionine, phenylalanine, proline, serine, threonine, tryptophan, tryosine, and valine. The peptides of the library have five amino acids, although peptides of fewer or greater amino acids in length may be made. Using 19 amino acids, about 2.5 million peptide sequences are possible ($19^5 = 2,476,099$).

A reaction vessel has 19 reaction chambers, one for each amino acid to be coupled in each chamber. Approximately 10 grams of polydimethylacrylamide resin are divided into about 0.5 gram quantities in each of the chambers of the reaction vessel. A mixing vessel is securely attached to the reaction vessel. The resin is washed nine times with dimethylformamide (DMF). The wash solvents are introduced through the filtered aperture in the chambers under control of a pair of solenoid valves switched to solvent position. Solvent is removed under pressure through the filtered aperture, also under control of solenoid valves, as described in Section 5.1, supra.

Activated amino acids are introduced to the fractions of solid supports in each chamber of the reaction vessel, again under control of the solenoid valves, which is switched to the reagent position.

After introduction, the set of first amino acids is completely coupled to substantially all the sites of the solid supports. As used herein, complete coupling means that the coupling reaction is driven to completion irrespective of the differences in the coupling rates of individual amino acids. In addition, the amino acids are coupled to substantially all available coupling sites on the solid support so that each solid support will contain essentially only one species of peptide. Complete coupling will result in solid support/first amino acid combinations.

The coupling of the amino acids may be accomplished by techniques familiar to those in the art and provided, for example, in Stewart and Young, 1984, Solid Phase Synthesis, Second Edition, Pierce Chemical Co., Rockford, Ill. As would be known to those of ordinary skill in the art, the process of peptide synthesis on solid supports generally involves building a peptide from the carboxyl or C-terminal end in which the C-terminal amino acid with its α-amino group protected is attached to a solid phase polymer. The protecting group is then cleaved off, and the next amino acid, also protected, is coupled by a peptide bond to the α-amino group of the amino acid attached to the solid support. The cycle of deprotection of the prior amino acid and coupling the additional amino acid is repeated until the peptide is completed. Any reactive side chains of the amino acids are protected by chemical groups that can withstand the coupling and $N^\alpha$-deprotection procedure but can be removed at the end of the synthesis.

In order to couple an amino acid to the growing synthetic chain, the carboxyl group of the blocked amino acid must be activated. Many methods of activation may be used in the practice of the invention and include, for example, preformed symmetrical anhydrides (PSA), preformed mixed anhydride (PMA), acid chlorides, active esters, and in situ activation of the carboxylic acid, as set forth in Fields and Noble, 1990, "Solid phase peptide synthesis utilizing 9-fluorenylmethoxycarbonyl amino acids", Int. J. Pept. Protein Res. 35:161–214.

The use of Fmoc amino acids is but one strategy of peptide synthesis. A Boc (t-butyloxycarbonyl-protected amino group) strategy may also be used to prepare a library of peptides bound to the solid support (e.g., Geysen et al., 1987, J. Immunol. Methods 102:259–274).

To ensure mixing, the solenoid valves controlling liquid and gas flow to the reaction chambers is opened to the gas input position, and inert gas (nitrogen or argon) is pumped in to agitate the reaction mixture. The valve on the mixing vessel is open to the exhaust position.

Preferably, the completeness of coupling should be assessed, although to minimize the large number of samples to be tested, it may be preferable to test coupling of difficult amino acids, e.g., valine and isoleucine. Those skilled in the art would be familiar with the well known quantitative monitoring tests such as ninhydrin (the Kaiser test), picric acid, 2,4,6-trinitrobenzenesulfonic (TNBS), fluorescamine, and chloranil, which are based on reagent reaction with free amino groups to produce a chromophobic compound. If imino acids (e.g., Pro and Hyp) are used, isatin monitoring is a preferred method. Fields and Noble, supra. Quantification of reaction completeness may be monitored during the course of the reaction, e.g., as described by Salisbury et al. (International Patent Publication No. WO91/03485) or using the acid-base indicator bromophenol blue, as described by Krchnak et al. (1988, Collection Czech. Chem. Commun. 53:2542–2548).

With Fmoc synthesis, the Kaiser test is preferred. In the Kaiser test, a sample from each tube can be tested with ninhydrin reagent obtained from Pierce Chemical in the method set forth by Sarin et al. (1981, Anal. Biochem. 117:147–157).

If the coupling reaction is incomplete as determined by this test, the reaction can be forced to completion by several methods familiar to those in the art, including (a) a second coupling using a one to five fold excess of protected amino acid, (b) an additional coupling using different or additional solvents (e.g., trifluoroethane), or (c) the addition of chaotropic salts, e.g., $NaClO_4$ or LiBr (Klis and Stewart, 1990, "Peptides: Chemistry, Structure and Biology," Rivier and Marshall, eds., ESCOM Publ., p. 904–906).

The last step of the coupling is to remove the reaction mixture and wash the beads as described above.

After the coupling reaction is complete the aliquots of the solid support/first amino acid combinations are thoroughly mixed. Thorough mixing occurs by filling the chambers of both the reaction vessel and the mixing vessel with DMF, and inverting both vessels to transfer the solid support to the mixing vessel. The solid supports are thoroughly mixed by bubbling gas, repeated inversion, agitation (shaking), or with a stirring device. The solid support/amino acids can be N-α-amino deprotected, e.g., by 20% piperidine (in a synthesis using Fmoc chemistry) in the mixing chamber. The solid support is then washed thoroughly as described above. The vessels are again inverted to allow the solid supports to redistribute into each of the 19 chambers of the reaction vessel. Substantially equal fractions of solid support/first amino acid combinations transfer to each of the chambers. A uniform distribution of each amino acid coupled to solid support is found in each chamber. The solid support/amino acids can be Nα amino-deprotected and washed if this step has not been performed, and a second set of activated amino acids introduced. Again, a single activated amino acid is introduced to each chamber. Since each chamber has all 19 solid support/amino acid combinations, after the reaction is complete, every possible first amino acid will be coupled to every possible second amino acid. Each solid support will have one dipeptide species. After the second coupling step, there will be 361 ($19^2$) different dipeptide combinations, each on a separate solid support.

The process is repeated five times total, so that a library of every possible pentapeptide sequence using 19 amino acids is obtained.

5.3 SYNTHESIS OF MANY COMPOUND SPECIES

The present apparatus provides for syntheses of a large variety of classes of compounds that can be prepared by the stepwise coupling of individual subunits. For example, the compound may be a peptide, an oligonucleotide, an oligosaccharide, a lipid, [other polymer species].

Standard synthesis reactions well known in the art are used to couple subunits to the solid support in the apparatus. Methods of synthesis of various compounds are taught in the following references, although the apparatus may be used for any stepwise solid phase synthetic method, as can be recognized:

Peptide synthesis—see Stewart and Young, 1984, *Solid Phase Peptide Synthesis*, Second Edition, Pierce Chemical Co., Rockford, Ill.

Oligonucleotide synthesis—see Caruthers, 1985, Science 230:281 and Caruthers et al., 1987, Methods in Enzymology 154:287–313.

Oligosaccharide synthesis—see Douglas et al., 1991, J. Am. Chem. Soc. 113:5095–5097.

Various references have been cited herein, the disclosures of which are incorporated herein in their entirety.

While the invention has been described in conjunction with specific embodiments, it is evident that numerous alternatives, modifications, and variations will be apparent to those skilled in the art in light of the description and are within the scope of the appended claims.

What is claimed is:

1. An apparatus for solid phase synthesis of compounds coupled to solid supports, comprising:
   (a) a reaction vessel having a plurality of identical separated reaction chambers for holding aliquots of solid supports coupled thereto and for carrying out isolated reactions of said aliquots, wherein each of the chambers has a substantially triangular cross-section, and each cross-section has a vertex adjacent to at least one vertex of all chambers, and each of the chambers has an opening;
   (b) a mixing vessel having a mixing chamber, wherein the mixing chamber has sufficient volume to hold all aliquots of solid supports of the reaction chambers and to permit uniform mixing of the aliquots;
   wherein the reaction vessel is attached to the mixing vessel forming a container arranged such that all openings of the chambers of the reaction vessel face the opening of the chamber of the mixing vessel as to permit transfer of aliquots of solid supports from the chambers of the reaction vessel to the chamber of the mixing vessel and to permit transfer of equal aliquots of uniformly mixed solid supports from the chamber of the mixing vessel back to the chambers of the reaction vessel.

2. The apparatus of claim 1 wherein each of the chambers of the reaction vessel has at least one aperture in addition to the opening.

3. The apparatus of claim 2 comprising a filter located at the aperture of each of the chambers to permit fluid to flow through the filter while retaining the solid support in the chamber.

4. The apparatus of claim 1 wherein the reaction vessel further comprises means for introducing fluid specific to each of the chambers and for removing liquid from each of the chambers.

5. The apparatus of claim 4 wherein each of the chambers of the reaction vessel comprises at least one valve to control the flow of fluid to and from each of the chambers.

6. The apparatus of claim 5 further comprising microcomputer means operatively connected to said at least one valve for controlling the operation of the valve.

7. The apparatus of claim 4 wherein the mixing vessel further comprises means for introducing fluid into the chamber of the mixing vessel and for venting the chamber.

8. The apparatus of claim 1 wherein the chamber of the mixing vessel has a circular cylindrical shape and the opening of the chamber forms one end of the circular cylindrical shape.

9. The apparatus of claim 1 wherein the chamber of the mixing vessel has at least one aperture in addition to the opening.

10. The apparatus of claim 9 comprising a filter located at the aperture of the chamber of the mixing vessel permitting fluid to flow through the filter while retaining the solid supports in the chamber.

11. The apparatus of claim 1 wherein the mixing vessel further comprises means for introducing fluid into the chamber of the mixing vessel and for venting the chamber.

12. The apparatus of claim 11 comprising at least one valve to control the flow of fluid to and from the chamber of the mixing vessel.

13. The apparatus of claim 12 further comprising microcomputer means operatively connected to said at least one valve for controlling the operation of the valve.

14. The apparatus of claim 1 further comprising a means to control temperature of the chambers of the reaction vessel.

15. The apparatus of claim 1 further comprising means to block at least one chamber of the reaction vessel when such chamber is not used.

16. An apparatus for solid phase synthesis of compounds coupled to solid supports, comprising:

(a) a container having a plurality of identical separated reaction chambers for holding aliquots of solid supports coupled thereto and for carrying out isolated reactions of said aliquots, each of the reaction chambers having substantially triangular cross-section, and each cross-section having a vertex adjacent to at least one vertex of all chambers, the container further having a mixing chamber that has sufficient volume to hold all aliquots of solid supports of the reaction chambers;

(b) means for introducing fluid to each of the reaction chambers of the container; and (c) means for controllably removing fluid from the container.

* * * * *